(12) United States Patent
Bensimon et al.

(10) Patent No.: US 6,225,055 B1
(45) Date of Patent: May 1, 2001

(54) APPARATUS FOR THE PARALLEL ALIGNMENT OF MACROMOLECULES, AND USE THEREOF

(75) Inventors: Aaron Bensimon, Antony; David Bensimon, Paris, both of (FR)

(73) Assignee: Institut Pasteur, Paris (FR)

( * ) Notice: Subject to any disclaimer, the term of this patent is extended or adjusted under 35 U.S.C. 154(b) by 0 days.

(21) Appl. No.: 09/011,242

(22) PCT Filed: Aug. 1, 1996

(86) PCT No.: PCT/FR96/01218

§ 371 Date: Apr. 2, 1998

§ 102(e) Date: Apr. 2, 1998

(87) PCT Pub. No.: WO97/06420

PCT Pub. Date: Feb. 20, 1997

(30) Foreign Application Priority Data

Aug. 3, 1995 (FR) .................................................. 95 09466

(51) Int. Cl.[7] ....................................................... C12Q 1/68
(52) U.S. Cl. .......................... 435/6; 435/283.1; 435/286.4; 435/287.2; 435/287.9; 435/307.1; 435/309.1
(58) Field of Search ............................... 435/283.1, 286.4, 435/287.2, 287.9, 307.1, 309.1, 309.6

(56) References Cited

U.S. PATENT DOCUMENTS 5,840,862 * 5/1999 Bensimon et al. .................. 536/22.1

* cited by examiner

*Primary Examiner*—Kenneth R. Horlick
*Assistant Examiner*—Janell E. Taylor
(74) *Attorney, Agent, or Firm*—Finnegan, Henderson, Farabow, Garrett & Dunner, LLP

(57) ABSTRACT

The present invention relates to an apparatus for the parallel alignment of macromolecules on the surface S of a solid support by displacement of a meniscus formed by the triple interface surface S/solution/air. The apparatus includes a container receiving a solution including the macromolecules to be aligned, a means for immersing the solid support into the solution, with the solid support surface configured to anchor macromolecules, and a means for the relative rectilinear displacement of the surface S and the surface of the solution to thereby cause motion of the meniscus and establish the parallel alignment of the macromolecules. The present invention also relates to a method for the parallel alignment of the macromolecules using the apparatus of the invention.

30 Claims, 2 Drawing Sheets

FIG_1
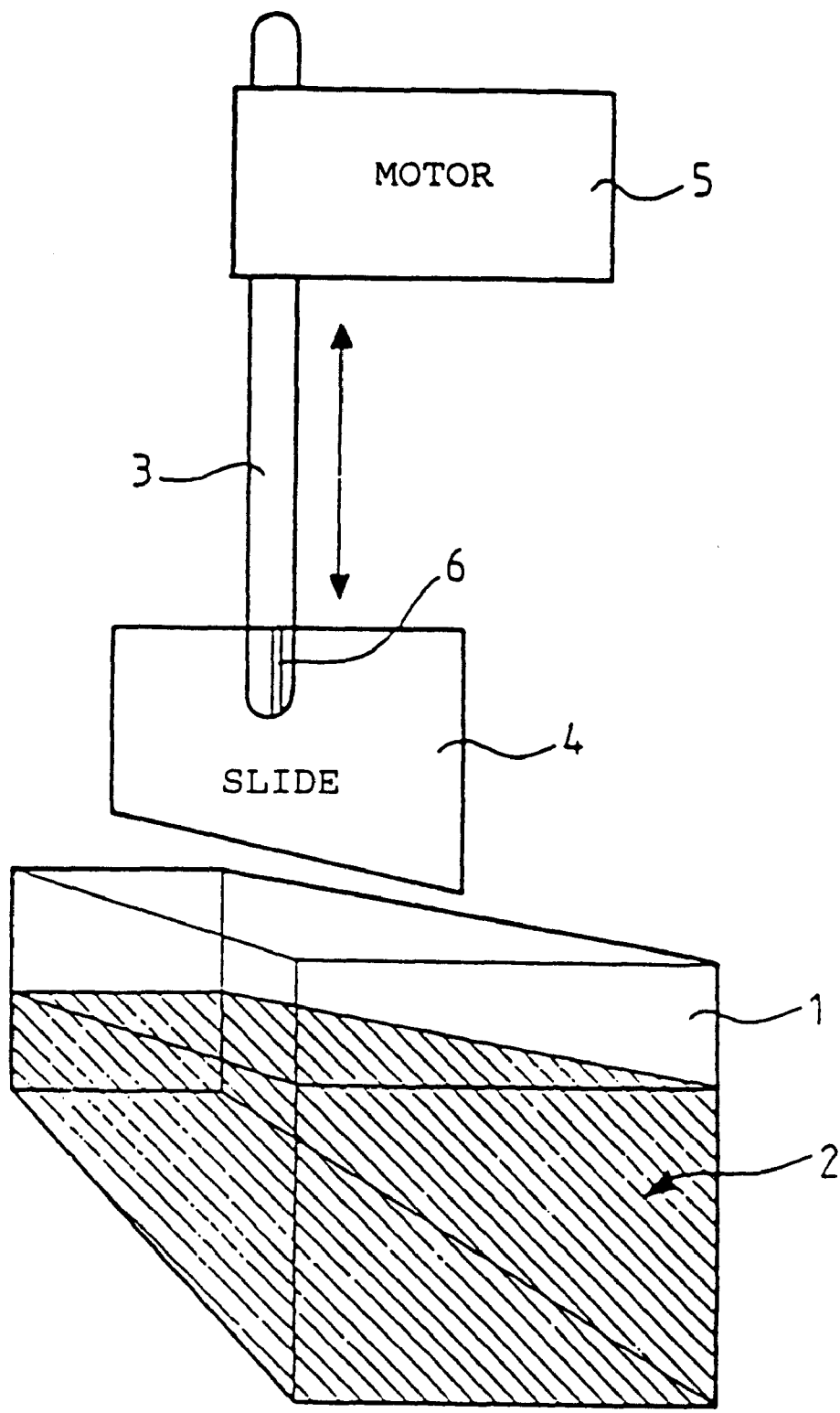

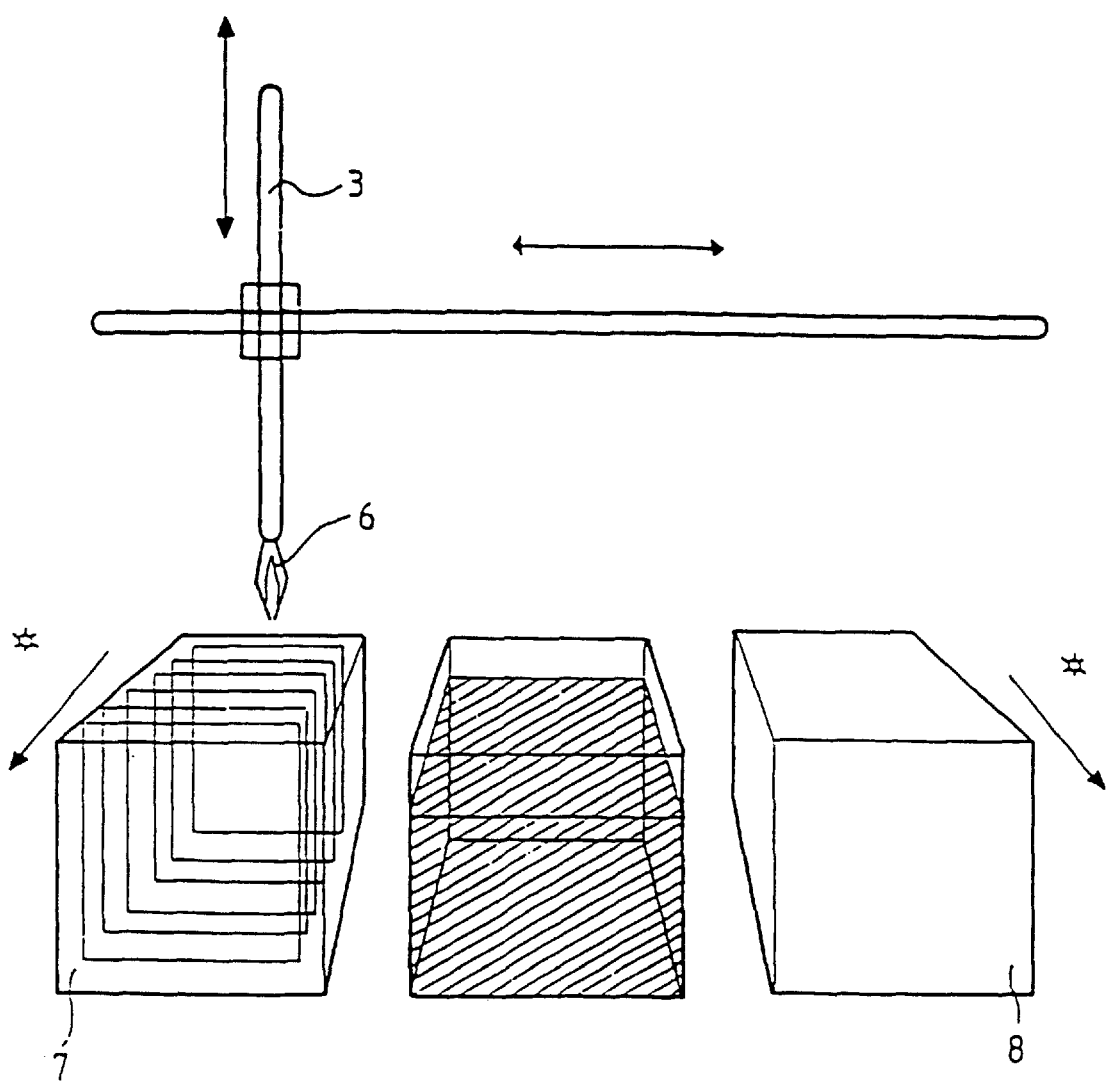
FIG_2
☆ Movement of the compartments by increments

APPARATUS FOR THE PARALLEL ALIGNMENT OF MACROMOLECULES, AND USE THEREOF

BACKGROUND OF THE INVENTION

The present invention relates to an apparatus for the parallel alignment of macromolecules on a solid support by the passage of a meniscus.

A process for the alignment of macromolecules, also called "molecular combing" has been described in the patent application in France No. 94 07444.

Controlling the conformation of macromolecules represents a major industrial challenge, for example in the manufacture of sensors or of controlled molecular assemblies, or alternatively in problems of detection and analysis. It may be useful to have an elongated molecular conformation. By way of example, in the case where polymers are grafted on a substrate, it has been proposed to extend them by the action of an electric field, a flow or with the aid of optical tweezers. In particular, in biology, the alignment of DNA—by electrophoresis (Zimmermann and Cox Nucl. Acid Res. 22, p 492, 1994), free flow (Parra and Windle, Nature Genetics, 5, p 17, 1993 and WO 93/22463) or in a gel (Schwartz et al. Science 262, p 110, 1993 and USP 33531) or with the aid of optical tweezers (Perkins et al., Science 264 p 819, 1994 and also U.S. Pat. No. 5,079,169)—opens numerous possibilities in mapping, or in the detection of pathogens.

These methods only allow in general an imperfect alignment, or alternatively a transient alignment—that is to say that relaxation of the molecule occurs once the stress disappears. In the case of optical tweezers, the method is expensive, is limited to only one molecule at a time, and is difficult to carry out by non-qualified staff.

A special technique for aligning DNA by flow after cell lysis, followed by drying, has been proposed (I. Parra and B. Windle and WO 93/22463). The alignment obtained is very imperfect and nonhomogeneous and numerous nonaligned masses are observed.

In Patent Application FR 94 07444, there has been described a novel and simple method for aligning macromolecules on the surface S of a support, characterized in that the triple line S/A/B (meniscus) resulting from the contact between a solvent A and the surface S and a medium B is caused to move on said surface S, said macromolecules having a part, especially an end, anchored on the surface S, the other part, especially the other end, being in solution in the solvent A.

It has been observed that the mere passage of a meniscus over molecules of which one part is anchored on a substrate, the remainder of the molecule existing freely in solution makes it possible to align them uniformly, perpendicularly to the moving meniscus, leaving them adsorbed on the surface behind the meniscus. This phenomenon is called "molecular combing" here.

More specifically, the stretching of the free part of the molecule is achieved by the passage of the triple line S/A/B constituting the meniscus between the surface S, the solvent A and a medium B which may be a gas (in general air) or another solvent.

In a specific embodiment, the meniscus is a water/air meniscus, that is to say that the solvent A is an aqueous solution and the medium B is air.

The movement of the meniscus can be achieved, in particular, by gradual evaporation of the solvent A or by a mechanical route by translation of the surface S.

To do this in Patent Application FR 94 07444, a drop of solvent containing the molecules to be aligned is placed between two supports of which at least one corresponds to said support of surface S and the meniscus is moved for example either by evaporation or by moving the two supports relative to each other.

By "support", there is understood any substrate whose cohesion is sufficient to withstand the passage of the meniscus.

The support may consist, at least at the surface, of an organic or inorganic polymer, a metal especially gold, a metal oxide or sulfide, a semiconductor element or an oxide of a semiconductor element, such as a silicon oxide or a combination thereof, such as glass or a ceramic.

There may be mentioned more particularly glass, superficially oxidized silicon, graphite, mica and molybdenum sulfide.

As "support", there may be used a single support such as a slide, beads, especially polymer beads, but also any form such as a bar, a fiber or a structured support, and also particles, whether it be powders, especially silica powders, which can moreover be made magnetic fluorescent or colored as known in the various assay technologies.

The support is advantageously in the form of cover slips.

Macromolecules, such as ordinary polymers, or biological polymers such as DNA, RNA or proteins, can be anchored by ordinary methods on a support.

The macromolecule to be aligned can be chosen from biological macromolecules such as proteins, especially antibodies, antigens, ligands or their receptors, nucleic acids, DNA, RNA or PNA, lipids, polysaccharides and derivatives thereof.

It was observed that the stretching force acts locally within the immediate vicinity of the meniscus. It is independent of the length of the molecule, of the number of molecules anchored, and within a wide range, of the speed of the meniscus. These characteristics are particularly important for aligning the molecules homogeneously and reproducibly.

It is possible to add surfactant elements into the solvent A, especially water, and/or the medium B, especially air, which modify the properties of the interfaces. The stretching can indeed be controlled by the addition of surfactants, or by an adequate surface treatment.

Too high a surface-macromolecule attraction (for example an excessively high level of adsorption) can interfere with the alignment of the molecules by the meniscus, these molecules remaining adsorbed at the surface in a state which is not necessarily stretched. Preferably, the surface exhibits a low rate of adsorption of said macromolecule, such that only the anchored molecules are aligned, the others being carried by the meniscus.

However, it is possible to vary the differences in adsorption between a part of the macromolecule, especially its ends, and its other parts (in particular for long molecules such as DNA or collagen) in order to anchor, by adsorption, the molecules by a part, especially their end(s) alone, the remainder of the molecule existing freely in solution, on a wide variety of surfaces and align them by the passage of the meniscus as described above.

The adsorption of a macromolecule onto a surface can be easily controlled by means of the pH or of the ionic medium content of the medium or of an electric voltage applied over the surface. The surface charges and the electrostatic (repulsive or attractive) interactions between the surface and the molecule are thus changed, thereby making it possible to pass from a state of complete adsorption of the molecule onto the surface to a total absence of adsorption. Between these two extreme cases, there is a range of control parameters where the adsorption occurs preferably through the end of the molecules and which will therefore be used advantageously to anchor them on the surface, and then to align them by the passage of the meniscus.

Once aligned, the molecules adhere strongly to the surface. In the case of DNA, it was possible to observe them by fluorescence several months after their alignment.

The technique therefore consists, in a first instance, in the anchoring, on the pretreated surface of a solid support in solution, of macromolecules, especially DNA, by their end (s). This specific anchoring—only the ends of the molecules adhere to the surface of the support—requires a precise control of certain physicochemical parameters of the solution: pH, temperature. This step is designated later by the name "incubation step". The duration of incubation has an influence on the rate of anchoring per unit of surface.

In a second instance, the system passes from the configuration: surface in solution, to a configuration: surface outside the solution. This passage was first achieved by natural evaporation of a drop of solution deposited on the pretreated surface. During the evaporation, the edge of the drop, which constitutes a meniscus, that is to say a triple interface: surface-solution-air, moves because of the reduction in the volume of the drop. The effect of the passage of the meniscus on the surface is a tensile force on the DNA molecules anchored on the surface, of which the consequence is their stretching in the direction of withdrawal of the meniscus, that is to say perpendicularly to the axis of the meniscus. The stretched molecules adhere to the surface in a durable manner. This step constitutes the actual molecular combing.

SUMMARY OF THE INVENTION

The apparatus according to the present invention makes it possible to carry out this second step in a different manner. Instead of using the withdrawal of the meniscus of a drop of water, which is roughly centripetal in the direction of the center of the drop, giving rise to a parallel alignment of the molecules only locally, a meniscus is used whose withdrawal causes a parallel alignment of the macromolecules over their entire length.

More precisely, the subject of the present invention is an apparatus for the parallel alignment of macromolecules on the surface S of a solid support by movement of a meniscus formed by the triple interface S/solution/air, characterized in that it comprises:

a container intended to receive a solution containing the macromolecules to be aligned, means for immersing said solid support in said solution, and means for relative rectilinear movement of the surface S and of the surface of said solution.

In one embodiment, the surface S may be withdrawn from the solution or conversely, the solution may be withdrawn from the surface S, the meniscus being in a relative movement.

Advantageously, said means for immersing the solid support and said means for relative rectilinear movement of the meniscus and of the surface S consist of means for vertical translation of said surface S perpendicularly to the surface of said solution.

In one embodiment, said means for vertical translation of said surface S comprise:

means for gripping the solid support, and guiding and motor means for causing translation of said gripping means along a vertical axis placed perpendicularly to said container.

In particular, said means for vertical translation of the surface S comprise:

means for gripping the solid support consisting of a vertical rod placed perpendicularly to said container and supporting means for pinching the solid support, and guiding and motor means for controlling the vertical translation of the rod between a low immersion position and a high withdrawn position.

Advantageously therefore, the apparatus according to the present invention comprises, in addition, especially when the solid support consists of a slide:

a first compartment for storing the solid supports, especially the slides, before immersion in said container, and a second compartment for storing the solid supports, especially the slides, on which the macromolecules are aligned after their withdrawal from said container.

In this case, it may comprise, in addition, means for successively presenting said slides perpendicularly to said first compartment of said container and to said second compartment.

In particular, when said compartments and said container are aligned, the apparatus comprises, in addition, guiding means and motor means to bring about the horizontal translation of the rod when it is in the raised position so as to allow said slides to be presented perpendicularly to said compartments and to said container.

The apparatus according to the present invention comprises numerous advantages:

perfect parallelism of the combed molecules over their entire length, the possibility of aligning macromolecules of size ranging up to 1200 kilobases whereas the drop evaporation process did not allow the alignment of molecules of size greater than 500 kilobases, the use of a volume of solution corresponding to the capacity of the reservoir allows the incubation of a practically unlimited number of slides (within the limit of chemical stability of the molecules in solution). It is indeed possible to sequentially incubate any number of slides when it is the slide which is withdrawn from the solution, as was the case in the process based on the evaporation of a drop of solution, any slide size, and more generally any support pretreated to allow anchoring of the molecules, can be used. It is indeed sufficient to adapt the volume of the reservoir to the support to be incubated, the incubation and stretching phases being dissociated, it is possible to vary the incubation time and the stretching rate independently, whereas these are more difficult to control in the drop evaporation process, in the case of a method of use where the solution is withdrawn from the reservoir, the slides remaining fixed, successive incubations of the slides can be performed in the same reservoir, but in different media.

The molecular combing apparatus according to the present invention thus makes it possible to pass from the basic research stage to that of applied research or even of standard laboratory instrumentation, as regards all the possible applications of molecular combing (mapping, diagnostic, and the like).

Appropriately, said means for moving the meniscus allow the movement of the meniscus at a speed of 10 to 100 µm/sec.

The speed of extraction of the slides from the solution has no influence on the stretching level of the combed molecules, in this speed range. This speed, which can undoubtedly be exceeded without influencing the quality of the combing, makes it possible to comb a pretreated glass cover slip of 22×22 mm$^2$ in less than five minutes.

Appropriately, the volume of said container is from 1 to 10 ml.

The volume of solution in the reservoir being notably larger than that of a drop (a few ml against a few tens of µl), it is possible to vary the temperature thereof without excessively increasing the evaporation level: we plan to study the influence of this parameter on the anchoring level of the molecules.

The pH of the solution is crucial for the specificity of the anchoring, as preliminary studies have shown. The apparatus according to the present invention advantageously comprises a system for controlling this parameter.

As such, the apparatus allows the serial combing of a large number of pretreated slides since the DNA solution contained in a reservoir of a few ml makes it possible to prepare a practically unlimited number thereof.

By "anchoring" of the macromolecule on the surface, there should be understood an attachment resulting from a chemical reactivity both through a covalent linkage and a noncovalent linkage such as a linkage resulting from physicochemical interactions, such as adsorption, as described above.

This anchorage of the macromolecule can be achieved directly on (or with) the surface, or indirectly, that is to say via a linkage such as another molecule, especially another molecule with biological activity. When the anchorage is achieved indirectly, the macromolecule can be grafted chemically on said linkage, or can interact physicochemically with said linkage, in particular when said intermediate linkage is a molecule with biological activity recognizing and interacting with said macromolecule.

In one embodiment, the macromolecule and said linkage are both molecules with biological activity which interact, such as an antigen and an antibody respectively, complementary nucleic acids or lipids. In these cases, the noncovalent attachment of the macromolecule consists of a linkage of the type: antigen-antibody, ligand-receptor, hybridization between complementary nucleic acid fragments or hydrophobic or hydrophilic interaction between lipids.

Advantage is thus taken of the very high specificity and the very high selectivity of certain biological reactions, especially antigen-antibody reactions, DNA or RNA hybridization reactions, interprotein reactions or avidin/streptavidin/biotin type reactions, as well as reactions of ligands and their receptors.

Thus, in order to carry out the direct or indirect anchoring of the macromolecule on the surface S, it is possible to use a solid surface having certain specificities. It is in particular possible to use certain pretreated surfaces which make it possible to attach certain proteins or DNA, whether modified or otherwise.

Such surfaces are commercially available (Covalink, Costar, Estapor, Bangs, Dynal for example) in various forms having at their surface COOH, NH$_2$ or OH groups for example.

It is, in this case, possible to functionalize the DNA with a reactive group, for example an amine, and carry out a reaction with these surfaces. However, these methods require specific functionalization of the DNA to be attached.

A technique allowing anchorage without prior treatment of the DNA has also been described. This process consists in causing a free phosphate at the 5' end of the DNA molecule to react with a secondary amine of the surface (NH Covalink surface).

Anchoring by adsorption can be achieved by adsorption of the end of the molecule by controlling the surface charge by means of the pH, the ionic content of the medium or the application of an electric voltage over the surface given the differences in adsorption between the ends of the molecule and its middle part. Nonfunctionalized DNA molecules were thus anchored, by way of example, on surfaces coated with molecules ending with a vinyl or amine group such as polylysine molecules, or various surfaces such as glass, coated with silane type molecules ending with vinyl or amine groups or alternatively glass cover slips previously cleaned in an acid bath. In this latter case, the surface of the glass indeed has SiOH groups.

It is also possible to functionalize the DNA with a first reactive group or a protein $P_0$ in order to cause it to react with a surface coated with a second reactive group or with a protein $P_1$, which are capable of reacting specifically with each other respectively, that is to say for example $P_1$ with $P_0$. The $P_0/P_1$ pair may be a pair of the type: biotin/streptavidin (Zimmermann and Cox) or digoxigenin/antibody directed against digoxigenin (anti-DIG) for example (Smith et al., Science 258, 1122 (1992)).

Preferably, the anchoring surfaces will have a low fluorescence level so as not to interfere with the detection of the molecules after their alignment, in particular if the detection is done by fluorescence.

A solid support having, under the reaction conditions, a surface having an affinity for only part of the macromolecule, the rest of the macromolecule remaining freely in solution, is preferably used.

In one embodiment, a solid support is used which has at the surface at least one layer of an organic compound having, outside the layer, an exposed group having an affinity for a type of molecule with biological activity which may be said macromolecule itself or a molecule recognizing and/or interacting with it.

The support can therefore have a surface coated with a reactive group or with a molecule with biological activity.

By "affinity", there should be understood both a chemical reactivity and an adsorption of any type, this under optional conditions of attachment of the molecules onto the exposed group, modified or otherwise.

In one embodiment, the surface is essentially compact, that is to say that it limits access by the macromolecule with biological activity to the bottom layers and/or to the support, this in order to minimize nonspecific interactions, and the other components of the layer exhibit little or no affinity for said macromolecules.

It is also possible to use surfaces coated with a reactive exposed group (for example NH$_2$, COOH, OH, CHO) or with a macromolecule with biological activity (for example: proteins, such as streptavidin or antibodies, nucleic acids such as oligonucleotides, lipids, polysaccharides and derivatives thereof) which is capable of attaching an optionally modified part of the molecule.

Thus, surfaces coated with streptavidin or with an antibody according to known processes ("Chemistry of Protein Conjugation and Cross-linking", S. C. Wong, CRC Press (1991)) are capable of attaching a macromolecule having, at a specific site, a biotin or an antigen.

Likewise, surfaces treated so as to have single-stranded oligonucleotides can serve in order to anchor on them DNAs/RNAs having a complementary sequence.

Among the surfaces having an exposed reactive group, there may be mentioned those on which the exposed group is a —COOH, —CHO, $NH_2$, —OH group, or a vinyl group containing a double bond —CH═$CH_2$ which is used as it is or which can be activated so as to give especially —CHO, —COOH, —$NH_2$ or OH groups.

The supports with highly specific surfaces can be obtained using various processes. There may be mentioned by way of example:

(A) a layer of carbon-containing, optionally branched, polymer at least 1 nm thick, having reactive groups as defined below and (B) surfaces obtained by depositing or anchoring on a solid support one or more molecular layers; the latter can be obtained by forming successive layers attached through noncovalent linkages, as nonlimiting example, Langmuir-Blodgett films, or by molecular self assembly, this allowing the formation of a layer attached by covalent linkage.

In the first case, the surface can be obtained by polymerization of at least one monomer generating at the surface of the polymer said exposed group, or alternatively by partial depolymerization of the surface of a polymer to generate said exposed group, or alternatively by deposition of polymer.

In this process, the polymer formed has vinyl linkages such as a polyene derivative, especially surfaces of the synthetic rubber type, such as polybutadiene, polyisoprene or natural rubber.

In the second case, the highly specific surface contains:

on a support, a substantially monomolecular layer of an organic compound of elongated structure having at least:

an attachment group having an affinity for the support, and an exposed group having no or little affinity for said support and said attachment group under attachment conditions, but optionally having, after chemical modification following the attachment, an affinity for one type of biological molecule.

The attachment can first of all be of the noncovalent type, especially of the hydrophilic/hydrophilic and hydrophobic/hydrophobic type, as in Langmuir Blodgett films (K. B. Blodgett, J. Am. Chem. Soc. 57, 1007 (1935).

In this case, the exposed group or the attachment group will be either hydrophilic or hydrophobic, especially alkyl or haloalkyl groups such as $CH_3$, $CF_3$, $CHF_3$, $CH_2F$, the other group being hydrophilic.

The attachment can also be of the covalent type, the attachment group will, in this case, react chemically with the support.

Certain surfaces of similar structure have already been mentioned in the electronic field, especially when the attachments are covalent, L. Netzer and J. Sagiv, J. Am. Chem. Soc. 105, 674 (1983) and U.S. Pat. No. 4,539,061.

Among the attachment groups, there must be mentioned more particularly the groups of the metal alkoxide or semiconductor type, for example silane, especially chlorosilane, silanol, methoxy- and ethoxysilane, silazane, as well as phosphate, hydroxyl, hydrazide, hydrazine, amine, amide, diazonium, pyridine, sulfate, sulfonic, carboxylic, boronic, halogen, acid halide, aldehyde groups.

Most particularly, as attachment group, groups capable of cross-reacting with an adjacent equivalent group, to give cross-linkages, will be preferably used; for example they will be derivatives of the metal alkoxide or semiconductor type, for example silane, especially dichlorosilane, trichlorosilane, dimethoxysilane or diethoxysilane and trimethoxy- or triethoxysilane.

The choice of the attachment group will obviously depend on the nature of the support; the silane-type groups are quite suitable for covalent attachment on glass and silica.

As regards the exposed groups, irrespective of the surface, they are preferably chosen from ethylenic groups, acetylenic groups or aromatic radicals, primary, tertiary or secondary amines, esters, nitriles, aldehydes, halogens. But they may be most particularly the vinyl group; indeed, the latter can be either chemically modified after attachment to give, for example, a carboxylic group or derivatives of carboxylic groups such as alcohol groups, aldehyde groups, ketone groups, acidic groups, primary, secondary or tertiary amines, or to give a pH-dependent direct anchoring of the biological macromolecules such as nucleic acids and proteins, without chemical modification of the surface or of the macromolecules.

Preferably, the chains connecting the exposed group to the attachment group are chains carrying at least 1 carbon atom, preferably more than 6 and in general from 3 to 30 carbon atoms.

As regards the support itself, the use of glass, surface-oxidized silicon, a polymer or gold with or without pretreatment of the surface, is generally preferred.

In the case of glass or silica, there can be used advantageously the known techniques for surface functionalization using silane derivatives, for example: Si—OH+$Cl_3$—Si—R—CH═$CH_2$ gives Si—O—Si—R—CH═$CH_2$, R consisting for example of $(CH_2)_4$. Such a reaction is known in the literature, with the use of ultrapure solvents. The reaction leads to a lawn of molecules having their C═C end at the surface exposed to the outside.

In the case of gold, this being optionally in the form of a thin layer on a substrate, the known techniques for surface functionalization use thiol derivatives, for example: Au+HS—R—CH═$CH_2$ gives Au—S—R—CH═$CH_2$, R consisting for example of $(CH_2)_4$. Such a reaction is described in liquid medium and leads, like the preceding trichlorosilane-silica reaction, to a lawn of molecules having their C═C end at the surface exposed to the outside.

The surfaces thus obtained are preferably coated with a macromolecule with biological activity chosen from:

proteins, nucleic acids, lipids, polysaccharides and derivatives thereof.

Among the proteins, there should be mentioned antigens and antibodies, ligands, receptors, but also products of the avidin or streptavidin type, as well as derivatives of these compounds.

Among the RNAs and DNAs, there should also be mentioned the α, β derivatives as well as the thio derivatives and mixed compounds such as PNAs.

It is also possible to attach mixed compounds such as glycopeptides and lipopolysaccharides for example, or alternatively other elements such as viruses, cells in particular, or chemical compounds such as biotin.

The attachment of the biological macromolecules may be covalent or noncovalent, for example by adsorption, hydrogen bonds, hydrophobic, ionic interactions, for example, in which case cross-linking can be advantageously carried out in the molecules grafted by known methods ("Chemistry of Protein Conjugation and Crosslinking", S. C. Wong, CRC Press (1991)) and this in order to enhance their cohesion.

As mentioned above, it is possible to have an exposed group which allows direct reaction with molecules with biological activity, but it is also possible to envisage that the exposed group is treated, after attachment, so as to be converted, as indicated above, to a hydroxyl, amine, alcohol, aldehyde, ketone, COOH radical or a derivative of these groups before attachment of the biological molecule.

When such groups were exposed, techniques for attachment of proteins and/or of DNA for example are known, they are indeed reactions used for surfaces which are already used for biological analyses, especially for Costar surfaces, Nunc surfaces or microbeads such as Estapor, Bang and Dynal for example, on which molecules of biological interest, DNA, RNA, PNA, proteins or antibodies for example, are anchored.

In the case where the exposed group is a —CH=CH$_2$ radical which is called hereinafter "surface C=C" or "surface with ethylenic bond", no document exists which mentions direct anchoring, in particular of DNA or of proteins. It has been demonstrated that these surfaces have a highly pH-dependent reactivity. This characteristic makes it possible to anchor the nucleic acids or the proteins using pH regions and often with a reaction rate which can be controlled by the pH.

The anchoring of DNA can be carried out by its end onto a surface having groups with ethylenic double bonds, by bringing the DNA into contact with the surface at a pH of less than 8.

In particular, the reaction is carried out at a pH of between 5 and 6, and is then stopped at pH 8.

Thus, for DNA at pH 5.5, the anchoring reaction is complete in one hour (if it is not limited by diffusion) and occurs via the ends. At pH 8, on the other hand, the attachment is very low (reaction rate of 5 to 6 orders of magnitude smaller). This pH dependent attachment effect specific for the ends, shows an improvement compared with the other surfaces which require functionalization of the DNA (biotin, DIG, NHS, and the like) or specific reagents (carbodiimide, dimethyl pimelidate) which form a peptide or phosphorimide linkage between —NH$_2$ and —COOH or —POOH.

It is also possible to carry out the anchoring of DNA by adsorption of its ends alone onto a surface coated with polylysine or a silane group ending with an amine group.

In order to carry out the anchoring of the DNA by its end on a surface coated with an amine group, the DNA is brought into contact with the surface at a pH of between 8 and 10.

It is possible to carry out the anchoring of DNA by its end to a glass surface pretreated beforehand in an acid bath, by bringing the DNA into contact with said surface at a pH of between 5 and 8.

Likewise, these surfaces can anchor proteins directly (protein A, anti-DIG, antibodies, streptavidin and the like). It has been observed that (i) the activity of the molecule can be preserved and (ii) that the reactivity of the prepared surface (initially C=C) is completely overshadowed in favor of the sole reactivity of the molecule of interest. It is therefore possible, starting with a relatively high initial reactivity, to pass to a surface having a very highly specific reactivity, for example that of specific sites on a protein.

By anchoring a specific antibody on the surface (for example anti-DIG), a surface is created whose reactivity is limited to the antigen (for example the DIG group). This indicates that the initial chemical groups have all been occulted by the antibodies grafted.

It is also possible to graft onto the reactive (chemically or biochemically) surfaces of other molecules with biological activity, especially viruses or other components: membranes, membrane receptors, polysaccharides, PNA, in particular.

It is also possible to attach the product of a reaction of biological interest (for example PCR) onto the prepared surfaces.

The apparatus according to the present invention allows the detection and/or the quantification of biological molecules, but also the measurement of intramolecular distance, the separation of certain biological molecules, especially a sample using antigen/antibody and/or DNA/RNA coupling techniques.

In particular, the apparatus according to the present invention can be used in a process for detecting a macromolecule consisting of a DNA sequence or a protein in a sample, in which:

the sample corresponding to solvent A, in which said macromolecule is in solution, is brought into contact with the surface of the support under conditions for forming a DNA/DNA, DNA/RNA hybrid or for forming the protein/protein reaction product, the hybrid or a macromolecule for labeling the hybrid or the reaction product being anchored in one part, the remainder being free in solution, it is stretched by the movement of the meniscus created by the contact between the solvent and the surface in order to orientate the hybrids or said labeling macromolecules and the measurement or the observation of the hybrids or of said labeling macromolecules thus orientated is carried out.

The passage of the meniscus, by stretching the molecules linearly, in the form of small rods, renders them more easily detectable if they are labeled. Moreover, these elongated molecules are stable to the open air and can be observed even after several months, without showing apparent degradation.

During a rehydration, the DNA molecules can remain adsorbed and elongated. Furthermore, it is possible to carry out a hybridization on the elongated molecule.

Furthermore, exhibiting a signal which is correlated and of uniform orientation by virtue of their stretching, these molecules are distinct from the surrounding noise. It is therefore easy to ignore the dusts, the inhomogeneities, which have no special spatial correlation. The alignment is also important because in solution, the molecules in the form of a pellet fluctuate thermally, thereby causing very high variations in their fluorescence signal gathered preferably with a small depth of field and limits their observation. The apparatus according to the present invention therefore allows the observation of isolated molecules with a very high signal to noise (S/N) ratio.

It is remarkable that this ratio is independent of the number of molecules anchored. The S/N ratio posed by the detection of a molecule is the same as that for 10,000. Furthermore, this stretching technique makes it possible to easily discriminate between molecules of varying lengths.

The stretched molecules can be revealed by various enzymological methods and the like, such as fluorescence, or the use of radioactive or nonradioactive probes. Their detection can be achieved by measuring a global signal (for example the fluorescence) or by individual observation of the molecules by optical fluorescence microscopy, electron microscopy, local probe methods (STM, AFM and the like).

Thus in general, for the detection, separation and/or assay of a molecule in a sample, a surface capable of specifically attaching said molecule is used, and the detection, separation or assay are carried out using a reagent, fluorescent or otherwise, which detects the presence of the attached molecule.

Among the reagents, there are fluorescent reagents and nonfluorescent reagents.

The fluorescent reagents contain fluorescent molecules, advantageously chosen to be long molecules of size greater than 0.1 μm and reacting specifically, directly or indirectly, with the pretreated surfaces. For example, a double-stranded DNA molecule labeled by means of fluorescent probes (ethidium bromide, YOYO, fluorescent nucleotides and the like) capable of anchoring directly via one or more ends on a surface optionally having a vinyl or amine type group and the like, especially by a judicious choice of the pH or of the ionic content of the medium or by application of an electric voltage over the surface.

It is also possible to use a special functionalization of the molecule (DIG, biotin and the like) in order to anchor it at one or more points on a surface having complementary sites (anti-DIG, streptavidin and the like).

Nonfluorescent reagents allowing the detection of molecules previously aligned according to the present invention may consist especially of beads or microparticles anchored via another molecule attached specifically, directly or indirectly, to the aligned molecule and having only a weak nonspecific interaction with the surface.

Depending on whether the desired molecule is detected directly by fluorescence or indirectly by means of the above reagents, the detection will be described as "direct detection" or "flag detection".

The detection of the number of aligned molecules can be carried out on a small number of molecules (typically 1 to 1000), by a low-noise macroscopic physical test requiring neither electron microscope nor radioactivity nor necessarily PCR.

The apparatus according to the present invention is capable of being used by persons having only limited laboratory experience.

The alignment and detection techniques can be used for numerous applications among which, but with no limitation being implied:

the identification of one or more elements of DNA or RNA sequence which can be advantageously used for the diagnosis of pathogens or the physical mapping of a genome. In particular, the techniques described above make it possible to obtain a physical map directly on genomic DNA without the intermediate use of a cloning stage. It is understood that the combed molecule having been stretched relative to its crystallographic length, relative measurements are carried out. It is thus possible to measure the size of DNA fragments and the distance between fragments, with a resolution of the order of 200 nm for optical methods or of the order of 1 nm by the use of near field methods such as AFM or STM, in order to visualize and measure the distance between probes on the aligned DNA.

This naturally leads to:

1) the detection of deletions, additions or translocations of genomic sequences, in particular in the diagnosis of genetic diseases (for example Duchenne's myopathy);
2) the identification of promoters of various genes by measuring the distance between the regulatory sequences and those expressed;
3) the localization of regulatory proteins by identifying their position along the DNA or the position of their target sequence;
4) the partial or complete sequencing by measuring the distance using near field microscopy (for example AFM or STM) between hybridized probes belonging to an oligonucleotide base of given length;

the PCR in situ on aligned DNAs;
the improvement of the sensitivity of ELISA techniques with the possibility of detecting a small number (possibly less than 1000) of immunological reactions.
5) the identification of regions of transcription of genes such as introns and exons, the distance between the introns and exons and the size of the introns and exons.

Thus, physical mapping can be carried out directly on a genomic DNA without the intermediate use of a cloning stage. The genomic DNA is extracted, purified, optionally cleaved with one or more restriction enzymes and then combed on surfaces according to the process of the present invention.

The position and size of the desired gene on the genomic DNA are then determined by hybridization with probes specific for said gene, especially extracted from parts of the complementary DNA (cDNA) of the product of said desired gene.

Similarly, by hybridizing a genomic DNA combed, then denatured with labeled total cDNA, the position, size and number of exons of the gene in question are identified.

The position of the gene having been determined as described above or being known, it is then possible to identify, by hybridization, the flanking sequences of the gene. For that, the procedure is advantageously carried out by hybridization with labeled probes, obtained for example from an oligonucleotide library, in order to identify two or more probes which hybridize on either side of the gene.

From this determination, it is then possible, by in situ PCR techniques, to amplify the fragment delimited by the flanking probes which can serve as primers for the reaction, which fragment may contain the desired gene with its regulatory regions which may be tissue- or development-specific.

The amplification of the desired gene then proceeds using known PCR techniques on the amplified fragment as described above, using primers which can be reached by the exons constituting the cDNA.

By the combing of genomic DNA and the like, it is also possible to determine, by hybridization, the presence or absence of sequences for regulating a specific proximal gene, from which the possible families of proteins for regulating this gene (for example: helix-loop-helix, zinc-finger, leucine-zipper) will be determined.

The specific reactions between particular DNA/RNA/PNA sequences and another molecule (DNA, RNA, protein) can occur before or after aligning the molecules according to the present invention.

Thus, in the field of genetic diagnosis and physical mapping, the known methods of FISH (Pinkel et al., Proc. Nat. Acad. Sci. USA 83, 2934 (1986)) are advantageously used to hybridize single-stranded oligonucleotides labeled with DNA first aligned, and then denatured. The revealing of the hybrids will be carried out using known techniques (fluorescence, microbeads and the like) with a resolution in the measurement of the distances ranging from 0.2 μm (optically) to 1 nm (by near field microscopy; AFM, STM and the like).

Alternatively, it is possible to first hybridize fluorescent marker DNAs with single-stranded DNA in solution, and then to align this construct by action of the meniscus after having converted it to double-stranded DNA and anchored it on an appropriate surface.

It is also possible to use the apparatus of the present invention for detecting the presence of a pathogen. By way of example, the procedure can be carried out in two different ways depending on whether the recognition reaction (hybridization, attachment of protein) occurs before or after alignment by the meniscus.

Thus, by way of example, one or several oligonucleotide probes are anchored in one or more regions of a surface. The hybridization of the potentially pathogenic DNA is carried out in situ under stringent conditions so as to anchor only the hybridized molecules. Their detection and quantification is carried out after alignment by the meniscus according to the present invention.

Alternatively, the potentially pathogenic DNA is first aligned, then denatured and hybridized with an oligonucleotide probe under stringent conditions. The detection of the hybrid is then carried out by known methods, especially by the FISH method, as described above.

Similarly, it is possible to detect the presence (or the absence) of a small number of molecules, such as proteins, lipids, sugars or antigens. A minor modification of the ELISA techniques will be advantageously carried out, the usual detection method being replaced by the detection of a fluorescent molecule aligned according to the present invention and coupled to one of the reagents of the ELISA reaction.

Moreover, as mentioned by K. R. Allan et al. (US 84 114), the genetic mapping can be carried out by measuring the size of DNA fragments. Now, the novel techniques for stretching molecules described above (stretching by meniscus) allows the length of the stretched molecules to be measured, and this on a very small sample (a few thousands of molecules).

It is for example possible, but with no limitation being implied, to carry out the procedure in the following manner: A DNA sample is fragmented (by means of restriction enzymes) stained with a fluorophore and then anchored on a surface. The molecules are then stretched by the meniscus and the size of the stretched fragments is determined by optical fluorescence microscopy with a resolution and a maximum size of the order of 1000 bp (0.3 $\mu$m).

For this purpose, but also if it is desired to align very long molecules ($\geq$10 $\mu$m), known techniques will be advantageously used in order to limit the degradation of long macromolecules during their handling (by hydrodynamic shearing).

The apparatus according to the present invention can be used in a process for aligning and detecting DNA in which the DNA is stretched by an alignment process according to the invention, then denatured and then hybridized with specific probes in order to determine the position or the size of one or more specific sequences.

The apparatus according to the present invention can also be used for carrying out a process for the physical mapping of a gene on a genomic DNA in which the DNA is aligned or detected according to a process of the invention.

In particular, the position and the size of the desired gene on the genomic DNA are determined by hybridization with probes specific for said gene to be mapped.

The apparatus of the present invention allows the implementation of a process for the diagnosis of a pathology related to the presence or the absence of a DNA sequence specific for the pathology in which an alignment process according to the invention is used.

Finally, the apparatus according to the present invention is used in a process for preparing a gene in which the position of said gene on the genomic DNA aligned by the process according to the invention is identified by means of a probe specific for said gene, the sequence of said gene is amplified by in situ PCR.

The apparatus of the present invention therefore makes it possible to carry out a process for replacing a gene in the genome of a eukaryotic cell by targeted insertion of a foreign gene prepared according to the above gene preparation process.

The targeted insertion can be carried out according to the techniques described in WO 90/11354 by transfecting eukaryotic cells with a vector containing said foreign DNA to be inserted flanked by two genomic sequences which are contiguous to the desired site of insertion in the recipient gene. The insert DNA may contain either a coding sequence, or a regulatory sequence. The flanking sequences are chosen so as to allow, by homologous recombination, depending on the case, either the expression of the coding sequence of the insert DNA under the control of the regulatory sequences of the recipient gene, or the expression of a coding sequence of the recipient gene under the control of a regulatory sequence of the insert DNA.

BRIEF DESCRIPTION OF THE DRAWINGS

The accompanying drawings, which are incorporated in and constitute a part of this specification, illustrate the preferred embodiments of the invention and, together with the description, serve to explain the principles of the invention. In the drawings, FIG. 1 is a schematic view of the apparatus for parallel alignment of macromolecules on a solid surface according to a preferred embodiment of the present invention; and FIG. 2 is a schematic view of an overall system for moving solid surfaces to and from various compartments, including the container holding the solution of macromolecules, according to another preferred embodiment of the present invention.

DESCRIPTION OF THE PREFERRED EMBODIMENTS

Other characteristics and advantages of the present invention will appear in the light of the following description made with reference to the accompanying FIGS. 1 and 2 in which there is represented an apparatus according to the invention schematically consisting of two parts (see FIG. 1):

a container (1) containing the solution of molecules to be combed (2), a vertical rod (3) comprising attachment means (6) capable of supporting one (or more) surface(s) (4) on which the combing has to take place, the rod being movable along a vertical axis perpendicularly to the container (1), a motor (5) which makes it possible to move the rod in vertical translation perpendicularly to the container (1).

The meniscus formed by the interface surface S/solution/air is rectilinear. It remains fixed when the vertical rod is moved and when the surface is gradually withdrawn from the solution, or when the solution is gradually withdrawn from the reservoir. The direction of stretching, perpendicular to the meniscus, is therefore parallel to the vertical axis, and uniform over the entire surface.

The combination of these two parts constitutes the basis of an apparatus which is designated by the name "elevator", with reference to the vertical translational movement of the slides.

As represented in FIG. 2, the apparatus advantageously comprises a first compartment for slides to be incubated (7), and a second compartment receiving the incubated slides on which DNA is combed (8). The rod (3) is equipped, at its low end, with a device for the simple attachment of the slides (6) ("jaw" or tweezer type), and a degree of freedom of horizontal translation simply has to be added to it in order to allow it to successively present itself perpendicularly to the compartments (7) and (8) of the container (1).

A "combing" cycle consists in:
(i) taking hold of the slides to be incubated,
(ii) translation above the reservoir,
(iii) descent into the reservoir and incubation,
(iv) removal of the slides from the reservoir,
(v) translation above the storage compartment,
(vi) deposition of the slides in a second compartment,
(vii) return to step (i).

It is possible to use, as compartment for storing the slides to be incubated, the same container which serves to store the slides during their physicochemical treatment, thereby simplifying the manipulations which the user has to perform.

The compartments (7) and (8) are equipped with means allowing their movement in horizontal translation so that when the rod (3) is perpendicular to the compartments, the compartment (7) presents the slide to be incubated, and the compartment (8) presents an empty space for receiving the slide on which the macromolecules are aligned.

EXAMPLE 1

Materials and Methods

The λ DNA and the monoclonal antibody (anti-DIG) are obtained from Boehringer-Mannheim. The trichlorosilanes are obtained from Roth-Sochiel. The fluorescent nucleic probes (YOYO1, YOYO3 and POPO1) are obtained from Molecular Probes. The ultraclean glass cover slips are obtained from Erie Scientific (ESCO) cover slips). The probes possess a reactive group (DIG, biotin and the like) capable of anchoring specifically on a surface according to the present invention (having for example as anchoring site an anti-DIG antibody or streptavidin). The detection of the anchoring reaction is carried out directly by detection of the fluorescence of the DNA molecule stained by fluorescent molecules (ethidium bromide, YOYO, fluorescent nucleotides).

Surface Treatment

Glass cover slips are cleaned for one hour by UV irradiation under an oxygen atmosphere (by formation of ozone). They are then immediately placed in a desiccator previously purged of traces of water by an argon stream. A volume of about 100 to 500 μl of the appropriate trichlorosilane ($H_2C=CH—(CH_2)_N—SiCl_3$ is introduced into the desiccator, from which the surfaces are removed after about 12 hours (n=6) or 1 hour (n=1). Upon taking out, the surfaces are clear and nonwetting.

The functional groups of these double bond surfaces ($H_2C=CH—$) can be converted to carboxyl groups (—COOH) by soaking the treated cover slips, as described above, for about ten minutes in a solution of 25 mg $KMnO_4$, 750 mg $NaIO_4$ in 1 l of water, then by rinsing them three times in ultrapure water.

The cover slips thus functionalized can react with proteins. A volume of 300 μm of an aqueous solution (20 μg/ml) of proteins (protein A, streptavidin and the like) is deposited on a cover slip functionalized into a ($H_2C=CH—$) group. This cover slip is incubated for about two hours at room temperature, then rinsed three times in ultrapure water. The surfaces thus treated are clear and wetting. The surfaces treated with protein A can then react with an antibody, for example an anti-DIG antibody, by incubating in a solution of 20 μg/ml of antibody.

Moreover, on the surfaces having carboxyl groups, it is possible to graft oligonucleotides having an amine end (—$NH_2$), 200 μl of a solution of MES (50 mM, pH 55), carbodiimide (1 mg/ml) and 5 μl of oligo-aminic (10 pmol/140 μl) are deposited on a carboxylated surface and incubated for about 8 hours at room temperature. The cover slip is finally rinsed three times in NaOH (0.4 M) and then four times in ultrapure water. The cover slips thus prepared can hybridize DNAs complementary to the anchored oligonucleotide.

Anchoring of Native DNA on a Double Bond Surface

A pretreated ($H_2C=CH—$) cover slip is immersed in a solution of 5 to 10 ml of fluorescence-labeled λ DNA (YOYO1, POPO1 or YOYO3, but without specific end) of varying concentration and in different buffers (total number of molecules<$10^7$). The preparation is incubated for about 10 to 15 minutes at room temperature in an atmosphere saturated with water vapor. In a 0.05 M MES buffer (pH=5.5), a virtually general anchoring of the DNA molecules is observed. In contrast, in a 0.01 M Tris buffer (pH=8), there is practically no anchored molecule (ratio>$10^6$). This dependence can make it possible to control the activation/deactivation of surfaces (with respect to DNA) via the pH.

Identical conditions are used to anchor a yeast YAC containing an insert of several human genes of a size of between 700 Kb and 1 Megabase.

Alignment and Detection of the Anchoring By the Action of the Meniscus

The action of the meniscus on the molecule is limited to its immediate vicinity. The part of the molecule in solution in front of the meniscus fluctuates freely and the part left stuck on the surface behind the meniscus is aligned in the direction of movement of the meniscus. The extension rate of the molecule is therefore uniform and independent of its size.

By transferring the preceding preparation to a dry atmosphere, the slide is withdrawn from the solution and the DNA molecules, anchored on the surface, are stretched perpendicularly to the meniscus. The capillary force on the DNA molecule (a few tens of picoNewtons) is indeed sufficient to completely stretch the molecule (greater than the entropic elasticity forces), but too weak to break the bond between the end of the molecule and the treated surface. The DNA having been fluorescence labeled, the stretched molecules can be individually and easily observed. The anchoring between the surface and the DNA being limited to the ends, it is also possible to stretch either DNAs of λ phage or of YAC (total length greater than 400 μm).

Specific anchoring and detection

By treating the surfaces as described above with a specific monoclonal antibody, it is possible to control their specificity very precisely. Thus, the specificity of anti-DIG treated surfaces was tested in relation to λ DNA hybridized with an oligonucleotide complementary to one of the Cos ends and possessing a digoxigenin group (DIG) and in relation to nonhybridized DNAs. In the first case, a virtually general extension of the anchored molecules, by the action of the meniscus, was observed. In the second case, only a few anchored DNA molecules (<10) were observed in the whole sample.

λ DNAs were also hybridized with oligonucleotides complementary to one of the COS ends and attached to carboxylated surfaces, as described above. To visualize the hybridization low-stringency conditions (pure water at 40° C.) should be used. Under high-stringency conditions (high salinity), the fluorescence of the YOYO1 probes disappears and the hybridized DNAs cannot be seen. It was also possible to align the DNAs thus hybridized by passage of the meniscus.

Dependence of the Stretching on the Surface Treatment

The histogram of the lengths of λ DNA grafted on different surfaces and then aligned by passage of the meniscus shows a well defined peak but which is different for the different surfaces. Thus, on surfaces coated with a silane which end with a vinyl group, the DNA is stretched up to about 20 to 24 µm, and on clean glass to about 19 µm and on glass surfaces previously treated with protein A and with anti-DIG, the stretching is 16 microns.

The stretching therefore depends on the surface treatment. On hydrophobic surfaces, the stretching will be much longer (vinyl, $NH_2$). On hydrophilic surfaces, there is virtually no stretching.

EXAMPLE 2

Combing of DNA Molecules on Different Surfaces

The molecular combing of DNA on glass surfaces treated in various ways was observed. Advantage is taken of the difference in adsorption between the ends of the molecule and the rest of the molecule. By absorbing positively charged polymers onto a glass surface, adsorption of negatively charged DNA molecules is enhanced, however when this charge is large, the DNA molecule is stuck over its entire length and the combing is impossible. But it is possible to modify the charge of the polymers adsorbed on the glass by modifying the pH (or salinity) conditions, indeed, the positive charges are carried for example by $NH_2$ groups which pass to the protonated state $NH_3^+$ for a pH below the pK of the corresponding base. In basic pH, the charges disappear and the surface no longer attracts DNA. By finely controlling the pH, it was observed that the DNA molecules in solution passed from a state where they are completely stuck to the surface to an intermediate phase where they are anchored only by their ends and then to a phase where the surface no longer has affinity for the DNA. In the intermediate phase, the molecular combing can be carried out.

Surfaces coated with a silane ending with an $NH_2$ group were studied for which there is observed complete sticking at pH<8, and combing for 8.5<pH<9.5. The number of combed molecules is maximum at pH=8.5 it is divided by 2 at pH=9 and by 4 at pH=9.5. The relative extension on this surface was also determined which corresponds to 1.26 in the histogram.

Surfaces coated with polylysine were also examined which exhibit similar attachment characteristics as regards the pH: combing region 8.5 and exhibiting a shorter relative extension: 1.08.

Finally, the same behavior was found on glass surfaces freshly cleaned in a hydrogen peroxide/concentrated sulfuric acid mixture. These surfaces are highly wetting and become rapidly contaminated; however, a combing region was observed between 5.5<pH<7.4 whereas the region of strong adsorption is situated at pH=4.5. The relative extension of the molecules corresponds to 1.12.

Uniform and Directional Alignment of YAC

1 µg of YAC previously stained in its agarose block by means of a YOYO1 fluorescent probe is heated to 68° C., agarased and then diluted in 10 ml of MES (50 mM pH 5.5). Two silanized cover slips (C=C surfaces) are incubated for 15 minutes in this solution and then removed at about 170 µm/sec. The YAC molecules are all aligned virtually parallel to the direction of removal of the cover slips. The integrity of the molecules thus aligned is better than by evaporation after deposition between two cover slips.

Hybridization of a Cosmid with a Combed YAC

A YAC stained with YOYO as previously described is anchored on a C=C surface and then aligned by the meniscus, during withdrawal of the cover slip from the solution. The probes (cosmids) are labeled by incorporation of a biotinylated nucleotide by the randon priming technique. The labeled probes (100 ng) and 5 µg of sonicated salmon sperm DNA (≈500 bps) are purified by precipitation in Na-acetate and ethanol, and then denatured in a formamide solution (50% formamide, 2% FFC, 10% dextran sulfate).

The combed YACs are denatured with 120 µl of denaturing solution (70% formamide, 2xSSC) on a hotplate at 86° C. for 6 minutes. The previously denatured probes (20 ng) are deposited on the cover slip in a hybridization solution (55% formamide, 2xSSC, 10% dextran sulfate) covered with a cover slip which is sealed with rubber cement. The hybridization is carried out overnight at 37° C. in a humid chamber.

The revealing of the hybrids is performed according to procedures known for in situ hybridizations on decondensed chromosomes (D. Pinkel et al., PNAS USA 83, 2934 (1986) and PNAS USA 85, 9138 (1988)).

Hybridized segments are then observed by fluorescence microscopy. This example demonstrates the possibility of detecting the presence of a gene on a DNA molecule, which can be used for diagnostic purposes or for physical mapping of the genome.

What is claimed is:

1. Apparatus for parallel alignment of macromolecules on a surface S of a solid support, comprising:
    a container configured to contain a solution including the macromolecules to be aligned,
    a solid support surface S configured to anchor said macromolecules,
    means for immersing said solid support in said solution to form a meniscus created by a triple interface of the surface S, the solution, and a medium surrounding the surface S and the solution, and
    means for moving the surface S in a rectilinear direction relative to a surface of said solution to thereby establish the parallel alignment of macromolecules on the surface.

2. Apparatus according to claim 1, wherein said means for immersing the support and said means for the relative movement of the meniscus and of the surface S consist of the same means for vertical translation of said surface S perpendicularly to the surface of said solution.

3. Apparatus according to claim 2, wherein said means for vertical translation of the surface S comprise:
    means for gripping the solid support, and
    guiding and motor means for causing translation of said gripping means along a vertical axis placed perpendicularly to said container.

4. Apparatus according to claim 3, wherein said means for vertical translation of the surface S comprise:
    means for gripping the solid support comprising a vertical rod placed perpendicularly to said container and supporting means for pinching the solid support, and
    guiding and motor means for controlling the vertical translation of the rod between a low immersion position and a high withdrawn position.

5. Apparatus according to claim 1, further comprising:
    a first compartment for storing a solid support before immersion in said container, and
    a second compartment for storing a solid support on which the macromolecules are aligned after their withdrawal from said container.

6. Apparatus according to claim 5, further comprising means for successively presenting said solid supports perpendicularly to said first compartment of said container and to said second compartment.

7. Apparatus according to claim 6, wherein said compartments and said container are aligned, and further comprising a guiding and motor means to bring about the horizontal translation of the rod when it is in the raised position so as to allow said solid supports to be presented perpendicularly to said compartments and to said container.

8. Apparatus according to claim 1, further comprising a device for controlling the pH in the solution contained in said container.

9. Apparatus according to claim 1, wherein said means for moving the meniscus allow the movement of the meniscus at a speed of 10 to 100 $\mu$m/sec.

10. Apparatus according to claim 1, wherein the volume of said container is from 1 to 10 ml.

11. Use of the apparatus according to one of claims 1 to 10 in a process for aligning a macromolecule (macromolecules) on the surface S of a support, in which the triple line S/A/B (meniscus) resulting from the contact between a solvent A and the surface S and a medium B is caused to move on said surface S, said macromolecules having a part, especially an end, anchored on the surface S, the other part, especially the other end, being in solution in the solvent A.

12. Use of an apparatus according to one of claims 1 to 8 in a process for detecting, separating and/or assaying a macromolecule in a sample, in which a process for alignment according to claim 11 is used in which a molecule with biological activity capable of recognizing said sample macromolecule becomes attached to the surface S, and in that the detection, separation or assay are carried out using a reagent, fluorescent or otherwise, which detects the presence of the attached molecule or said macromolecule.

13. Use of the apparatus according to claim 12 in a process for detecting a macromolecule consisting of a DNA sequence or a protein in a sample, according to claim 10, characterized in that:
the sample corresponding to solvent A, in which said macromolecule is in solution, is brought into contact with the surface of the support under conditions for forming a DNA/DNA, DNA/RNA hybrid or for forming the protein/protein reaction product,
the hybrid or the reaction product being labeled and anchored in one part, the remainder being in solution, it is stretched by the movement of the meniscus created by the contact between the solvent and the surface in order to orientate the macromolecules and the measurement or the observation of the macromolecules thus orientated is carried out.

14. Use of an apparatus according to one of claims 1 to 10 in a process for the physical mapping of a gene on a genomic DNA in which the DNA is aligned and/or detected according to one of claims 11 to 13.

15. Use of an apparatus according to claim 13 for carrying out a process for the diagnosis of a pathology linked to the presence or absence of a given DNA sequence specific for said pathology.

16. Use of an apparatus according to one of claims 11 to 13 for carrying out a process for preparing a gene in which the position of said gene on the aligned genomic DNA is identified with the aid of a probe specific for said gene and the sequence of said gene is amplified by in situ PCR.

17. A method of using the apparatus of claim 1 for aligning a macromolecule on the surface S of the solid support, said method comprising the steps of:

(A) providing the surface S having a part of the macromolecule anchored on the surface S;
(B) contacting the surface S with a solvent A and a medium B to form a triple line S/A/B (meniscus); and
(C) moving the meniscus to align the macromolecule on the surface S.

18. The method according to claim 17, wherein the part of the macromolecule anchored on the surface is an end of the macromolecule.

19. A method of using the apparatus of claim 1 for detecting a macromolecule in a sample, said method comprising the steps of:
(A) providing a surface having a biologically active molecule aligned on the surface, the biologically active molecule being capable of recognizing the macromolecule in the sample;
(B) contacting the macromolecule in the sample with the aligned biologically active molecule under hybridizing conditions; and
(C) detecting attachment between the biologically active molecule and the macromolecule in the sample.

20. The method of using the apparatus according to claim 19, wherein detection of attachment is carried out using a labeling reagent capable of detecting the macromolecule in the sample or the biologically active molecule.

21. The method of using the apparatus according to claim 20, wherein the labeling reagent is fluorescent.

22. A method of using the apparatus of claim 1 for separating a macromolecule in a sample, said method comprising the steps of:
(A) providing a surface having a biologically active molecule aligned on the surface, the biologically active molecule being capable of recognizing the macromolecule in the sample;
(B) contacting the macromolecule in the sample with the aligned biologically active molecule under hybridizing conditions; and
(C) separating the macromolecule in the sample from the remainder of the sample.

23. A method of using the apparatus of claim 1 for assaying a macromolecule in a sample, said method comprising the steps of:
(A) providing a surface having a biologically active molecule aligned on the surface, the biologically active molecule being capable of recognizing the macromolecule in the sample;
(B) contacting the macromolecule in the sample with the aligned biologically active molecule under hybridizing conditions; and
(C) assaying the macromolecule in the sample.

24. The method of using the apparatus according to claim 19, wherein the macromolecule in the sample, the biologically active molecule, or both the macromolecule in the sample and the biologically active molecule are DNA or RNA.

25. The method of using the apparatus according to claim 19, wherein the macromolecule in the sample, the biologically active molecule, or both the macromolecule in the sample and the biologically active molecule are a protein.

26. A method of using the apparatus of claim 1, for physically mapping a gene, said method comprising the steps of:
(A) providing a surface having genomic DNA aligned on the surface;
(B) contacting the aligned genomic DNA under hybridization conditions with a sample containing a nucleic acid sequence capable of hybridizing with the genomic DNA; and (C) detecting hybridization between the aligned genomic DNA and the nucleic acid sequence in the sample.

27. A method of using the apparatus of claim 1 for diagnosing a pathology, said method comprising the steps of:
   (A) providing a surface having a nucleic acid sequence aligned on the surface, wherein said nucleic acid sequence is associated with the pathology;
   (B) contacting the aligned nucleic acid sequence under hybridization conditions with a sample containing DNA from a patient;
   (C) detecting hybridization between the aligned nucleic acid sequence and the DNA from the patient; and
   (D) correlating the detection of hybridization with the pathology.

28. A method of using the apparatus of claim 1 for amplifying a nucleic acid sequence, said method comprising the steps of:
   (A) providing a surface having the nucleic acid sequence aligned on the surface;
   (B) contacting the aligned nucleic acid under hybridization conditions with two or more oligonucleotide probes, which hybridize on opposing ends of the nucleic acid sequence; and
   (C) amplifying the nucleic acid sequence.

29. The apparatus according to claim 5, wherein the solid support is a slide.

30. A method of using the apparatus of claim 1 for aligning a macromolecule on the surface S of the solid support, said method comprising the steps of:
   (A) providing the surface S having a part of the macromolecule anchored on the surface S;
   (B) contacting the surface S with a solvent A and a medium B to form a triple line S/A/B (meniscus); and
   (C) moving the meniscus to align the macromolecule on the surface S, wherein said means for moving the meniscus allows the movement of the meniscus at a speed of 10 to 100 $\mu$m/sec.

* * * * *

UNITED STATES PATENT AND TRADEMARK OFFICE
CERTIFICATE OF CORRECTION

PATENT NO. : 6,225,055 B1
DATED : May 1, 2001
INVENTOR(S) : Aaron Bensimon et al.

It is certified that error appears in the above-identified patent and that said Letters Patent is hereby corrected as shown below:

Title page,
Item [57], last line, please replace "30 Claims, 2 Drawing Sheets" with -- 24 Claims, 2 Drawing Sheets --.

Claims,
Please delete claims 11-30, at col. 19, line 19 - col. 22, line 18, and insert in place thereof the following:

-- 11. A method of using the apparatus of claim 1 for aligning a macromolecule on the surface S of the solid support, said method comprising the steps of:

(A) providing the surface S having a part of the macromolecule anchored on the surface S;

(B) contacting the surface S with a solvent A and a medium B to form a triple line S/A/B (meniscus); and (C) moving the meniscus to align the macromolecule on the surface S.

12. The method according to claim 11, wherein the part of the macromolecule anchored on the surface is an end of the macromolecule.

13. A method of using the apparatus of claim 1 for detecting a macromolecule in a sample, said method comprising the steps of:

(A) providing a surface having a biologically active molecule aligned on the surface, the biologically active molecule being capable of recognizing the macromolecule in the sample;

(B) contacting the macromolecule in the sample with the aligned biologically active molecule under hybridizing conditions; and (C) detecting attachment between the biologically active molecule and the macromolecule in the sample.

UNITED STATES PATENT AND TRADEMARK OFFICE
CERTIFICATE OF CORRECTION

PATENT NO.   : 6,225,055 B1
DATED        : May 1, 2001
INVENTOR(S)  : Aaron Bensimon et al.

It is certified that error appears in the above-identified patent and that said Letters Patent is hereby corrected as shown below:

14. The method of using the apparatus according to claim 13, wherein detection of attachment is carried out using a labeling reagent capable of detecting the macromolecule in the sample or the biologically active molecule.

15. The method of using the apparatus according to claim 14, wherein the labeling reagent is fluorescent.

16. A method of using the apparatus of claim 1 for separating a macromolecule in a sample, said method comprising the steps of:

(A) providing a surface having a biologically active molecule aligned on the surface, the biologically active molecule being capable of recognizing the macromolecule in the sampe;

(B) contacting the macromolecule in the sample with the aligned biologically active molecule under hybridizing conditions; and (C) separating the macromolecule in the sample from the remainder of the sample.

17. A method of using the apparatus of claim 1 for assaying a macromolecule in a sample, said method comprising the steps of:

(A) providing a surface having a biologically active molecule aligned on the surface, the biologically active molecule being capable of recognizing the macromolecule in the sample;

(B) contacting the macromolecule in the sample with the aligned biologically active molecule under hybridizing conditions; and (C) assaying the macromolecule in the sample.

18. The method of using the apparatus according to claim 13, wherein the macromolecule in the sample, the biologically active molecule, or both the macromolecule in the sample and the biologically active molecule are DNA or RNA.

UNITED STATES PATENT AND TRADEMARK OFFICE
CERTIFICATE OF CORRECTION

PATENT NO. : 6,225,055 B1
DATED : May 1, 2001
INVENTOR(S) : Aaron Bensimon et al.

It is certified that error appears in the above-identified patent and that said Letters Patent is hereby corrected as shown below:

19. The method of using the apparatus according to claim 13, wherein the macromolecule in the sample, the biologically active molecule, or both the macromolecule in the sample and the biologically active molecule are a protein.

20. A method of using the apparatus of claim 1, for physically mapping a gene, said method comprising the steps of:

(A) providing a surface having genomic DNA aligned on the surface;

(B) contacting the aligned genomic DNA under the hybridization conditions with a sample containing a nucleic acid sequence capable of hybridizing with the genomic DNA; and (C) detecting hybridization between the aligned genomic DNA and the nucleic acid sequence in the sample.

21. A method of using the apparatus of claim 1 for diagnosing a pathology, said method comprising the steps of:

(A) providing a surface having a nucleic acid sequence aligned on the surface, wherein said nucleic acid sequence is associated with the pathology;

(B) contacting the aligned nucleic acid sequence under hybridization conditions with a sample containing DNA from a patient;

(C) detecting hybridization between the aligned nucleic acid sequence and the DNA from the patient; and (D) correlating the detection of hybridization with the pathology.

22. A method of using the apparatus of claim 1 for amplifying a nucleic acid sequence, said method comprising the steps of:

(A) providing a surface having the nucleic acid sequence aligned on the surface;

(B) contacting the aligned nucleic acid under hybridization conditions with two or more oligonucleotide probes, which hybridize on opposing ends of the nucleic acid sequence; and (C) amplifying the nucleic acid sequence.

UNITED STATES PATENT AND TRADEMARK OFFICE
CERTIFICATE OF CORRECTION

PATENT NO. : 6,225,055 B1
DATED : May 1, 2001
INVENTOR(S) : Aaron Bensimon et al.

It is certified that error appears in the above-identified patent and that said Letters Patent is hereby corrected as shown below:

23. The apparatus according to claim 5, wherein the solid support is a slide.

24. A method of using the apparatus of claim 1 for aligning a macromolecule on the surface S of the solid support, said method comprising the steps of:

(A) providing the surface S having a part of macromolecule anchored on the surface S;

(B) contacting the surface S with a solvent A and a medium B to form a triple line S/A/B (meniscus); and (C) moving the meniscus to align the macromolecule on the surface S, wherein said means for moving the meniscus allows the movement of the meniscus at a speed of 10 to 100 µm/sec. --

Signed and Sealed this

Sixteenth Day of April, 2002

Attest:

JAMES E. ROGAN
*Director of the United States Patent and Trademark Office*

*Attesting Officer*